US010789961B2

(12) United States Patent
Noh et al.

(10) Patent No.: US 10,789,961 B2
(45) Date of Patent: Sep. 29, 2020

(54) APPARATUS AND METHOD FOR PREDICTING/RECOGNIZING OCCURRENCE OF PERSONAL CONCERNED CONTEXT

(71) Applicant: ELECTRONICS AND TELECOMMUNICATIONS RESEARCH INSTITUTE, Daejeon (KR)

(72) Inventors: Kyoung Ju Noh, Daejeon (KR); Ji Youn Lim, Daejeon (KR); Ga Gue Kim, Daejeon (KR); Seung Eun Chung, Daejeon (KR); Hyun Tae Jeong, Daejeon (KR)

(73) Assignee: ELECTRONICS AND TELECOMMUNICATIONS RESEARCH INSTITUTE, Daejeon (KR)

(*) Notice: Subject to any disclaimer, the term of this patent is extended or adjusted under 35 U.S.C. 154(b) by 118 days.

(21) Appl. No.: 16/219,443

(22) Filed: Dec. 13, 2018

(65) Prior Publication Data

US 2019/0371344 A1 Dec. 5, 2019

(30) Foreign Application Priority Data

May 31, 2018 (KR) ........................ 10-2018-0062753

(51) Int. Cl.
*G10L 17/26* (2013.01)
*G06F 3/00* (2006.01)
(Continued)

(52) U.S. Cl.
CPC ............ *G10L 17/26* (2013.01); *A61B 5/0533* (2013.01); *G06K 9/00302* (2013.01);
(Continued)

(58) Field of Classification Search
CPC ............... G10L 17/26; G06F 3/00; G06F 9/00
See application file for complete search history.

(56) References Cited

U.S. PATENT DOCUMENTS 8,775,186 B2* 7/2014 Shin .................. G10L 17/26 704/270.1
2014/0234815 A1* 8/2014 Jang .................... A61B 5/165 434/236

(Continued)

FOREIGN PATENT DOCUMENTS

KR 1020020018541 A 3/2002
KR 1020120045415 A 5/2012

*Primary Examiner* — Shreyans A Patel

(57) ABSTRACT

Disclosed is technology for providing a proper UI/UX through various devices or services when occurrence of registered concerned context is predicted or recognized in order to predict or recognize the circumstances that require attention or emotion control with regard to a change in his/her biological information With this, a user designates his/her own biological information range or emotional state with regard to circumstances which catch his/her attention, and registers concerned context by selectively designating attributes of circumstantial elements. Further, a user registers feedback desired to be given and an external device/service desired to interface with when the occurrence of the concerned context is predicted or recognized. According to the attributes of the circumstances designated in the registered concerned context, points in time for collecting and managing UX data are automatically determined, thereby processing and managing the UX data as useful information.

19 Claims, 7 Drawing Sheets

(51) Int. Cl.
*G06F 9/00* (2006.01)
*A61B 5/053* (2006.01)
*G06K 9/00* (2006.01)
G10L 15/22 (2006.01)
A61B 5/0205 (2006.01)
H04W 88/18 (2009.01)
A61B 5/16 (2006.01)

(52) U.S. Cl.
CPC ............ *A61B 5/0205* (2013.01); *A61B 5/165* (2013.01); *G10L 2015/228* (2013.01); *H04W 88/18* (2013.01)

(56) References Cited

U.S. PATENT DOCUMENTS

| | | | |
|---|---|---|---|
| 2014/0280296 A1* | 9/2014 | Johnston | G06F 9/453 |
| | | | 707/769 |
| 2015/0182130 A1* | 7/2015 | Utter, II | A61B 5/681 |
| | | | 600/483 |
| 2016/0078061 A1* | 3/2016 | Hilsdale | G16H 40/20 |
| | | | 707/687 |
| 2017/0032168 A1* | 2/2017 | Kim | G06F 3/0414 |
| 2018/0249966 A1* | 9/2018 | Lewis | A61B 5/7275 |

\* cited by examiner

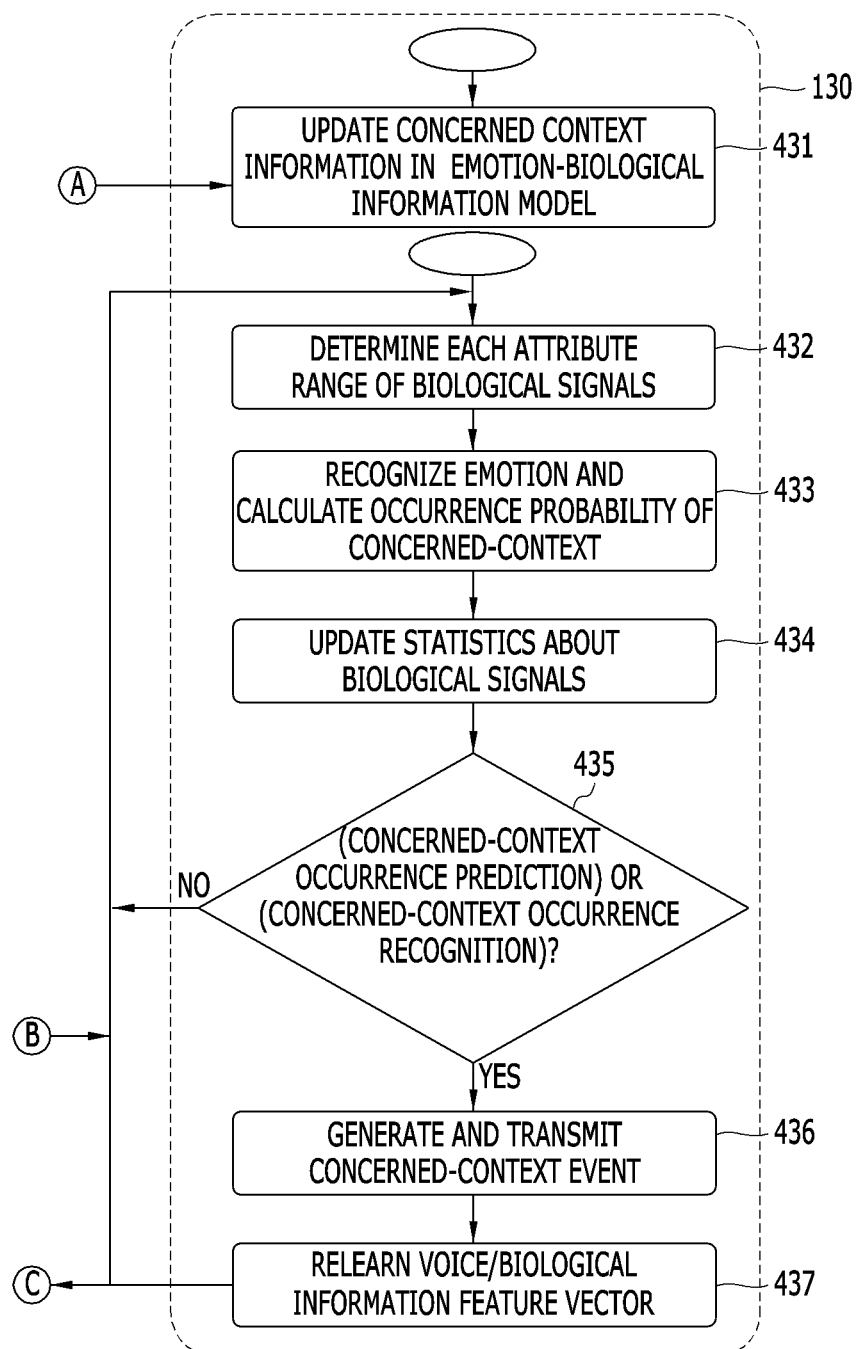

APPARATUS AND METHOD FOR PREDICTING/RECOGNIZING OCCURRENCE OF PERSONAL CONCERNED CONTEXT

CROSS-REFERENCE TO RELATED APPLICATION

This application claims priority to and the benefit of Korean Patent Application No. 10-2018-0062753, filed on May 31, 2018, the disclosure of which is incorporated herein by reference in its entirety.

BACKGROUND

1. Field of the Invention

The present invention relates to technology for giving a user a feedback on concerned context through various devices or services when occurrence of registered concerned context is predicted or recognized under a condition that the user has designated his/her own biological information, emotional state, and attributes of circumstances (time, place, behavior, etc.) and has registered the concerned context that requires attention or emotion control with regard to the designated attributes.

2. Discussion of Related Art

Researches and development have been steadily carried out on life-logging for providing a useful service to a user by storing and analyzing personal daily experience data. The life-logging based service has recently been required to provide a function of actively improving the quality of physical and emotional life to a user based on his/her experience data as well as a simple function of monitoring a user's behavior or setting an alarm. That is, when a user needs to control emotions or be careful about a change in his/her biological information (e.g., a biological signal), there is a need of providing a proper UI (user interface)/UX (user experience) suitable for a time and space in which the user is present. Further, there is a need of determining a proper point in time to process the experience data, and extracting and managing information useful for grasping personal characteristics from the continuously generated experience data.

Human emotions are closely related to their voice and/or biological information. For example, in the case of a negative emotional state such as an angry state, voice becomes louder, a tone becomes higher, a heart rate increases, breathing becomes faster, body temperature rises, and/or tension in muscles increases as compared to those in a usual state. Further, in the case of a negative emotional state such as a depressed state, a user voice generally features slow speaking, a long pause, small pitch variation, and a low amplitude.

In addition, the voice and/or the biological information are closely correlated with an ambient temperature and a user's specific behaviors such as sitting down, walking, standing up, running, sleeping, his/her specific utterance, etc. For example, a user's heart rate and breathing rate in a dynamic state such as walking or running become faster than those in a static state such as sitting down or standing up, and voice features are also changed in between. For example, a user's pulse rate may measure higher than usual when she/he gets emotionally excited, but strenuous exercise or high atmospheric temperature may also make the pulse rate become higher. As an example of a correlation between the atmospheric temperature and the biological information, blood vessels beneath a human skin is dilated at a high temperature and skin temperature rises, thereby causing a biological response of giving off body heat. In other words, a heart increases the amount of blood circulated beneath the skin and causes a rapid pulse and an increased cardiac output, thereby making a heartbeat rapid.

Therefore, not only the correlation between the emotion and the voice and/or the biological information but also the correlation among the user behavior, the atmospheric temperature, and the voice and/or the biological information have to be taken into account in order to accurately recognize the emotional state among pieces of information about the concerned context registered by a user. Further, such features have to be extracted and managed based on personal experience information since they largely vary depending on individuals.

SUMMARY OF THE INVENTION

An aspect of the present invention is to provide a proper UI/UX through a feedback as desired by a user by learning-based prediction or recognition of circumstances, which requires physical or emotional attention, registered by the user based on his/her experience data from real-life environments.

The present invention is conceived to solve the above problems, and directed to proposing technology for providing a UI/UX through various devices or services when occurrence of registered concerned context is predicted or recognized under a condition that a user has designated his/her own biological information range, emotional state, and circumstances such as time, place, behavior, etc. to be registered as the concerned context in order to predict or recognize the circumstances that require attention or emotion control with regard to a change in his/her biological signal (biological information).

With the apparatus and method for predicting/recognizing occurrence of personal concerned context according to one embodiment of the present invention, a user designates his/her own biological information range or emotional state with regard to circumstances which catch his/her attention, and registers concerned context by selectively designating attributes of circumstantial elements such as time, place, behavior, atmospheric temperature, etc. Further, a user registers a feedback desired to be given and an external device/service desired to interface with when the occurrence of the concerned context is predicted or recognized. Depending on the match between the current circumstance and the attributes of the circumstances designated in the registered concerned context, points in time for collecting and managing UX data are automatically determined, thereby processing and managing the UX data as useful information. Further, a personal emotion-biological information model of the present invention is configured to be robust to influences of a user behavior and an atmospheric temperature while recognizing his/her biological information range and emotional state, thereby having functions for generating, configuring and managing the personal emotion-biological information model capable of predicting and recognizing the occurrence of the registered concerned context.

Further, a mode of predicting/recognizing occurrence of personal concerned context is provided to calculate an occurrence probability of the concerned context by automatically recognizing a user's biological information range and emotion on the basis of experience data feature information of the collected voice and biological information (i.e., a biological signal) and generate and interface a concerned context occurrence prediction or recognition event according to the calculated occurrence probability.

According to one aspect of the present invention, there is provided an apparatus for predicting/recognizing occurrence of personal concerned context, the apparatus including: a UI device including a concerned context definer through which a user designates biological information, emotions, and circumstances and registers concerned context about the user's own biological information change or emotional state; and an emotion-biological information model management module including an emotion-biological information model manager which reflects information about the concerned context registered by the user in an emotion-biological information model, makes the emotion-biological information model learn from a user voice/biological information feature and reference statistics of the user voice/biological information feature depending on user behavior and atmospheric temperature, and manages the emotion-biological information model, and a concerned-context event generator which generates a concerned-context occurrence prediction event or a concerned-context occurrence recognition event by predicting or recognizing the occurrence of the concerned context registered in the concerned context definer of the UI device. According to one embodiment, the reference statistics about a voice feature depending to the user behavior and the atmospheric temperature may include maximum, minimum, average, deviation, or similar information about the voice/biological information feature extracted either in a frequency domain such as a pitch or in a time domain such as speaking rate (tempo) or change in amplitude of energy.

A user may designate a change in "biological information," states of "emotions," and attributes of "circumstances" such as time, place, user behavior, and atmospheric temperature, etc. to thereby register, modify, and manage a specific concerned context $c_k$ which requires his/her attention or is desired to be controlled. For example, a user may designate the concerned context to be registered by him/her, with a concerned context label (in the form of a descriptive text set by a user) such as "increasing heart rates in a crowded place", "angry at conversation", etc.

For example, as shown in the following Table 1 (with sorts of concerned context, elements, and user-designated attributes), an absolute time range based on the universal standard time or semantic attributes such as 'morning', 'afternoon', or 'evening' may be designated as "attributes of time", i.e., elements that belong to "circumstances" in the concerned context $c_k$. Further, an absolute address or semantic attributes such as 'home', 'street', and 'public place' may be designated as "attributes of place" in the circumstances. In addition, general behaviors such as 'sitting down', 'lying down', 'walking', 'running', etc. or specific behaviors such as 'sleeping', 'conversation', 'utterance of specific words', etc. may be designated as "attributes of user behavior".

TABLE 1

| Sort | Elements | Examples of attributes designated by user |
|---|---|---|
| Circumstances | Time | Morning, afternoon, evening |
| | Place | Address, home, street, public place |
| | Atmospheric temperature | — |
| | Behavior | Sitting down, standing up, walking, running, conversation, sleeping, specific utterance |

TABLE 1-continued

| Sort | Elements | Examples of attributes designated by user |
|---|---|---|
| Biological information | Heart rates HRV GSR Respiration volume Body temperature | Lower, normal, higher, regular, irregular |
| Emotions | Voice/biological information features | Neutral, positive, negative |

The elements included in the "biological information" include a heart rate (HR), a heart rate variation (HRV) calculated based on heartbeat information, a galvanic skin response (GSR), a respiration volume, a body temperature, etc., and the attributes such as 'normal', 'lower', 'higher', 'regular', 'irregular', etc. may be designated to these elements.

Further, the elements included in the "emotion" include a voice feature and a biological information feature, and the attributes such as 'neutral', 'positive' and 'negative' may be designated to these elements. In addition, detailed attributes corresponding to emotions such as sadness, anger and the like may be designated to 'negative'.

Meanwhile, for the registration of the concerned context and the configuration of the personal emotion-biological information model, a set C of concerned contexts $c_k$ registered by a user, a set S of elements $s_n$ in each circumstance, a set B of biological information (or biological signals) $b_m$, and a set E of recognized emotion labels $e_j$ may be defined by the following Table 2.

TABLE 2

| | |
|---|---|
| Set of concerned contexts $c_k$ | $C = \{c_1, c_2, \ldots, c_k\}, k \le K$ |
| Set of elements $s_n$ of circumstance | $S = \{s_1, s_2, \ldots, s_n\}, n \le N$ |
| Set of biological signals $b_m$ included in biological information | $B = \{b_1, b_2, \ldots, b_m\} m \le M$ |
| Set of recognized emotion labels $e_j$ | $E = \{e_1, e_2, \ldots, e_j\}, j \le J$ |

When a user registers the concerned context, there is no limit to ways of designating the detailed attributes of each element. For example, a user may not designate the attributes of a place or specific biological information range, but designate an attribute of 'morning' as the element of time in the concerned context, an attribute of 'conversation' as the element of user behavior, and an attribute of 'negative' as the element of emotion, thereby registering the concerned context with a concerned context label of "negative emotion at conference."

According to one embodiment of the present invention, the UI device may further include a circumstance extracting and recognizing unit which extracts a current circumstance received from the UI device or a user wearable information collection device, and recognizes whether concerned context designated with a circumstance matching the extracted current circumstance has been registered; and a voice/biological information feature extractor which extracts a voice/biological information feature from current user voice/biological information and transmits the extracted voice/biological information feature along with the circumstance to the emotion-biological information model management module when the circumstance extracting and recognizing unit recognizes that the current circumstance matches the circumstance of the registered concerned context.

According to one embodiment of the present invention, the UI device may further include a feedback registration unit which registers a type of feedback desired to be given when the concerned-context occurrence prediction or recognition event is generated; and a feedback giver which gives the registered type of feedback when the concerned-context occurrence prediction or recognition event is received from the emotion-biological information model management module.

According to one embodiment of the present invention, the UI device may further include an external device/service registration unit which registers an external device and service to interface with the feedback given when the concerned-context occurrence prediction or recognition event is generated.

According to one embodiment of the present invention, the emotion-biological information model management module may further include an emotion recognizer which extracts a feature vector to be used for recognizing the user's emotion from the voice/biological information feature received from the UI device; and a concerned-context occurrence probability calculator which calculates an occurrence probability of the concerned context on the basis of the emotion-biological information model and the extracted voice/biological information feature vector.

According to one embodiment of the present invention, the concerned-context event generator of the emotion-biological information model management module may use a threshold for determining occurrence prediction and a threshold for determining occurrence recognition so as to determine either of concerned-context occurrence prediction or concerned-context occurrence recognition.

According to another aspect of the present invention, there is provided an apparatus for predicting/recognizing occurrence of personal concerned context, the apparatus including: a concerned context definer through which a user designates biological information, emotions, and circumstances and registers concerned context about the user's own biological information change or emotional state; an emotion-biological information model manager which reflects information about the concerned context registered by the user in an emotion-biological information model, makes the emotion-biological information model learn from a user voice/biological information feature and reference statistics of the user voice/biological information depending on user behavior and atmospheric temperature, and manages the emotion-biological information model; and a concerned-context event generator which generates a concerned-context occurrence prediction event or a concerned-context occurrence recognition event by predicting or recognizing the occurrence of the concerned context registered in the concerned context definer.

According to still another aspect of the present invention, there is provided a method of predicting/recognizing occurrence of personal concerned context, the method including: by a user, designating biological information, emotions, and circumstances and registering concerned context about the user's own biological information change or emotional state; reflecting information about the concerned context registered by the user in an emotion-biological information model, making the emotion-biological information model learn from at least one of user voice and biological information features and reference statistics of user biological information feature depending on user behavior and atmospheric temperature, and managing the emotion-biological information model; and generating a concerned-context occurrence prediction event or a concerned-context occurrence recognition event by predicting or recognizing the occurrence of the registered concerned context.

The configuration and effect of the present inventive concept introduced as above will become apparent by the detailed description set forth herein with reference to the accompanying drawings.

BRIEF DESCRIPTION OF THE DRAWINGS

The above and other objects, features and advantages of the present invention will become more apparent to those of ordinary skill in the art by describing exemplary embodiments thereof in detail with reference to the accompanying drawings, in which:

FIG. 6A and FIG. 6B are flowcharts showing operations of a system for predicting/recognizing occurrence of concerned context.

DETAILED DESCRIPTION OF EXEMPLARY EMBODIMENTS

Figure 1:
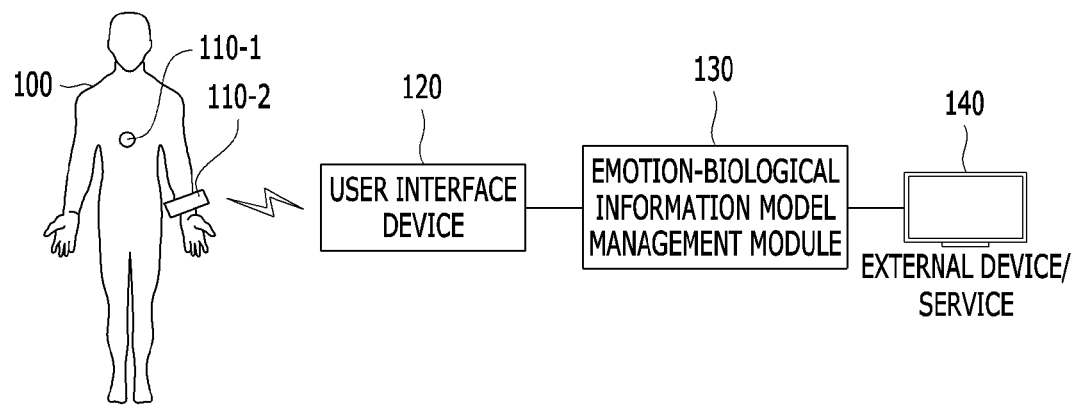
FIG. 1 is a conceptual view of a system for predicting/recognizing occurrence of personal concerned context.

FIG. 1 is a schematic configuration view for explaining a detailed embodiment of an apparatus and method for predicting/recognizing occurrence of personal concerned context according to the present invention. This embodiment includes information collection devices 110-1 and 110-2 attached to, worn on, or carried by a user 100, a user interface (UI) device 120 such as a smart phone, etc., and an emotion-biological information model management module 130 configurable in an additional independent server (including a cloud server) and installable even in the UI device 120.

Through the UI device 120, the user 100 may register concerned context in the form of a label (or a descriptive text) by designating his/her own concerned context label, specific biological information range, emotional state, and attributes of circumstances such as time, place, behavior, etc., and modify and manage the concerned context.

In the concerned context registered by the user 100, information collectable through the information collection devices 110-1 and 110-2 includes biological response information such as a heartbeat, heart rate variation (HRV), galvanic skin response (GSR), respiration volume, body temperature, etc. and circumstances such as a user behavior, etc. (a user's behavior information is collectable using an acceleration sensor or the like as the information collection device). Further, if a wireless microphone is used as the information collection devices 110-1 and 110-2, it is possible to collect a user's voice (actually, the UI device 120 is capable of autonomously collecting the voice). One or a plurality of information collection devices 110-1 and 110-2 may be employed, and therefore the voice, the biological information, the circumstance, etc. of the user 100, which are collected in each of the devices 110-1 and 110-2, may also be collected as one or a plurality of signals (e.g., a voice signal, a biological signal, a motion signal, etc.). In the present invention, there are no limits to the position at which the information collection device acquires information, the number of devices, and the kind of information to be collected.

The UI device 120 determines whether the circumstances such as time, place, user's behavior, atmospheric temperature, etc., which are extracted from data received from the information collection devices 110-1 and 110-2 or which the UI device 120 autonomously detects, match the attributes of circumstantial elements in the concerned context registered by the user 100.

Further, the UI device 120 extracts at least one of a voice feature and a biological information feature (hereinafter, referred to as a 'voice/biological information feature') from at least one of the voice and the biological response information of the user (hereinafter, referred to as 'voice/biological response information') which are detected from the data received from the information collection devices 110-1 and 110-2 or which the UI device 120 autonomously detects; and transmits the voice/biological information feature, along with the extracted or detected circumstance, to the emotion-biological information model management module 130. In this case, a user's voice/biological information feature extracted by the UI device 120 is sampled in units of a predetermined window $Win_{thr}$ (see FIG. 4 and its explanation). For example, the voice feature includes a feature in a frequency domain, such as mel-frequency cepstrum coefficients (MFCC), and a feature in a time domain, such as an amplitude, a speaking rate, an emphasis, pitch variability, utterance duration, a pause time, etc. of a voice. Likewise, each biological information feature is also sampled in units of the window $Win_{thr}$ (see FIG. 4 and its explanation). For example, the biological information feature may include the maximum, minimum, average, deviation and similar features in a time section.

The emotion-biological information model management module 130 automatically recognizes a user's biological information range and emotional state from the circumstance and the voice/biological information feature received from the UI device 120 on the basis of an already learned emotion-biological information model (e.g., a user's emotional state is inferable from the emotion-biological information model has been learned with the voice, biological information, and circumstance of the user), and calculates a probability of occurrence of concerned context so as to recognize the occurrence of the registered concerned context (when the concerned context has already occurred) or predict the occurrence of the registered concerned context (when the concerned context is going to occur or gradually completing the occurrence). Thus, when the occurrence of the registered concerned context is predicted or recognized, an occurrence prediction event or an occurrence recognition event (hereinafter, also inclusively referred to as 'the concerned context occurrence event') of the corresponding concerned context is generated and transmitted to the UI device 120 and/or an external device/service 140 such as a personal computer (PC), an artificial intelligence (AI) device, an Internet-of-things (IoT) device, other dedicated devices, a social media service, or the like registered by a user with regard to the corresponding concerned context, or a registered service interface is called. The concerned context occurrence event involves the identifier of the corresponding concerned context, the occurrence prediction or recognition time, and the type identifiers of the occurrence prediction event/occurrence recognition event.

Figure 2:
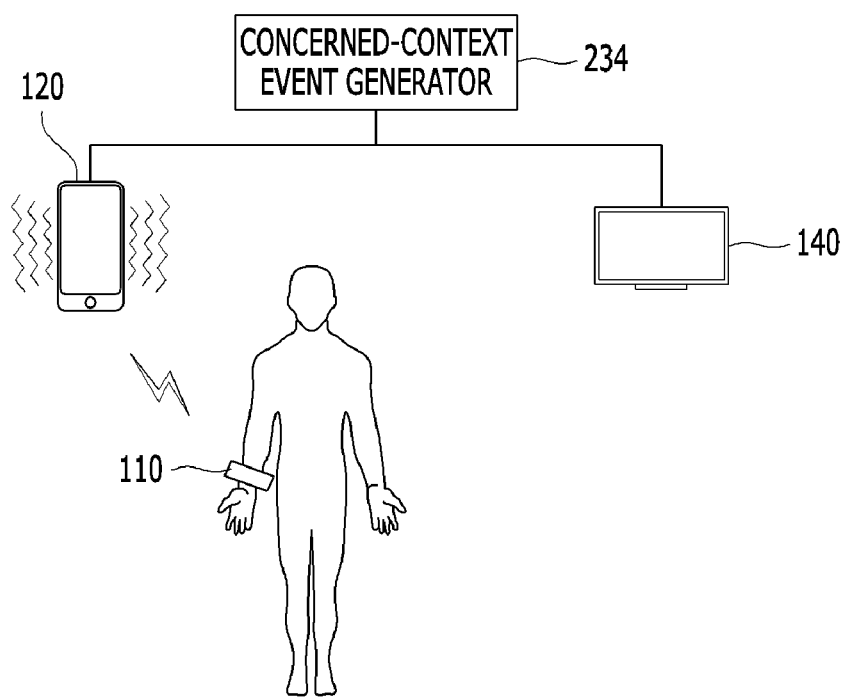
FIG. 2 is a conceptual view of service in a system for predicting/recognizing occurrence of personal concerned context.

FIG. 2 illustrates a service concept of an apparatus and method for predicting/recognizing occurrence of personal concerned context according to one embodiment of the present invention. Basically, a user registers concerned context and uses a learned emotion-biological information model to receive feedback on the occurrence of the concerned context through his/her own interface device (e.g., a smartphone, etc.) or an external device/service registered by him/her when the occurrence prediction or recognition event of the concerned context occurs.

Referring to FIG. 2, a service scenario according to one embodiment of the present invention will be described in detail. First, it will be assumed that a user registers a circumstance, in which a range of heartbeat biological information is higher than usual and an emotional state is 'negative' in a 'room (place)' at 'night (time)', with a concerned context label of 'a cautionary circumstance about a heartbeat and an emotion', and designates/registers the concerned context to be posted on an information posting board of a certain social media service (corresponding to an external device/service 140) along with vibration and text display in the UI device 120 as feedback to be received when the occurrence prediction or recognition event is generated.

When a specific element (e.g., a concerned-context event generator 234) of a module for managing the emotion-biological information model (See 130 in FIG. 1) generates a concerned context occurrence prediction or recognition event, this event is transmitted to the UI device 120. Therefore, a user receives feedback, which is given in the form of the vibration and the text registered by him/her, through the UI device 120 (or through the information collection device 110) and thus can predict or recognize the occurrence of the corresponding concerned context. Further, the user can call a registered external service interface (for example, a social media service information posting board) and check the occurrence of the concerned context through his/her external device 140.

In such a manner, a user receives a UI/UX for feedback suitable to a time and space that s/he is in, through the UI device 120 and/or the external device/service 140 in accordance with types (occurrence prediction or recognition) of a concerned context event that occurs in the emotion-biological information model management module 130.

Figure 3:
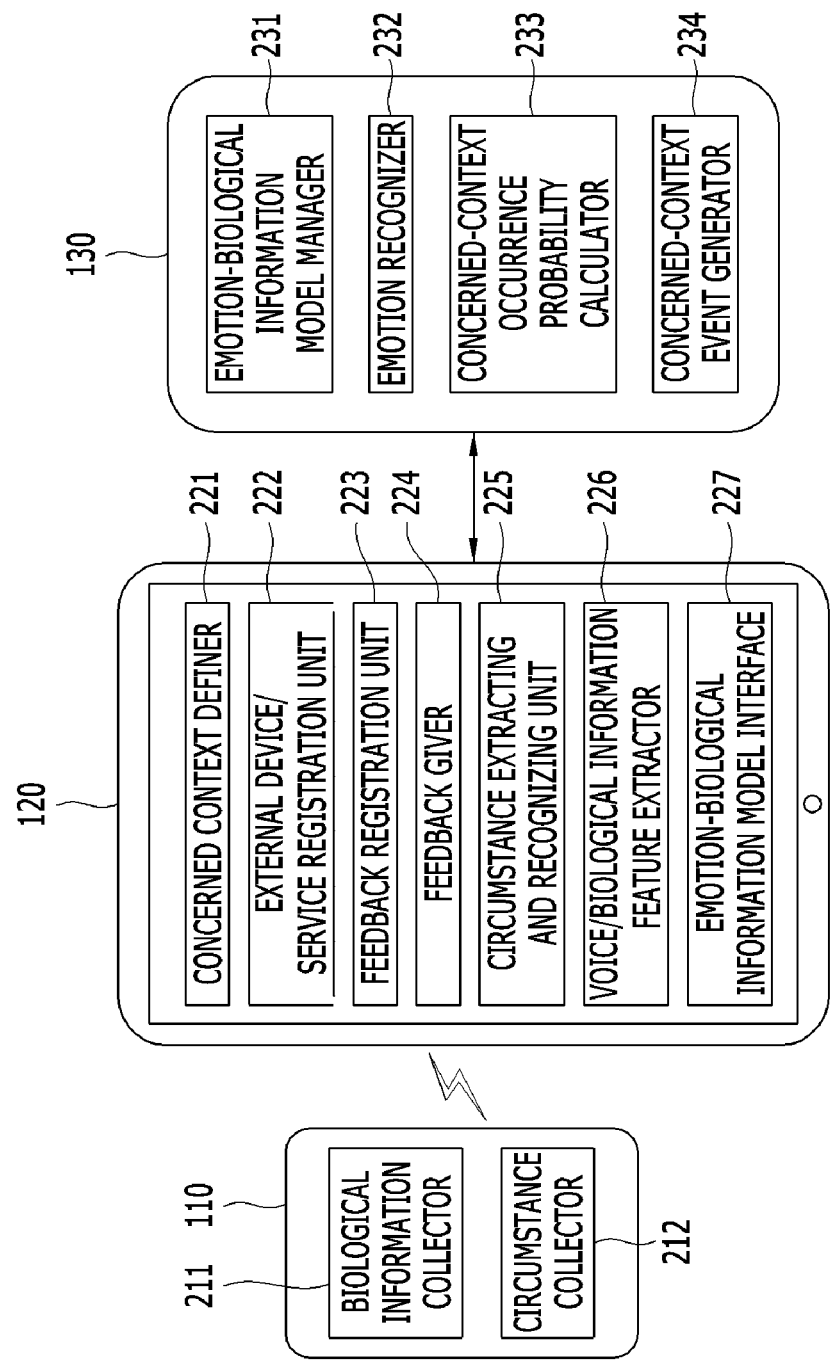
FIG. 3 is a view illustrating functional elements in a system for predicting/recognizing occurrence of personal concerned context.

FIG. 3 is a configuration view of an apparatus and method for predicting/recognizing occurrence of personal concerned context according to one embodiment of the present invention. Elements illustrated in FIG. 3 and the following drawings and descriptions refer to process performing steps in light of a method invention, but may also refer to process performing materializers in light of an apparatus invention.

The information collection device 110 includes a biological information collector 211 for collecting biological information by detecting a biological signal such as a heartbeat, an HRV, a GSR, a respiration volume, a body temperature, etc. from a user's body. According to another embodiment, the information collection device 110 may additionally include a circumstance collector 212 for collecting circumstances about behaviors such as a user's walking, running, lying down, sleeping, specific utterance, etc.

Through a concerned context definer 221 of the UI device 120 (e.g., a personal portable terminal such as a smartphone or the like), a user may perform functions of registering, modifying and deleting the concerned context. Further, through an external device/service registration unit 222, a user can register and manage the external device/service 140 for interfacing feedback to be received when a prediction or recognition event corresponding to the occurrence of the concerned context is generated. For the registration, an address of an external device or an application programming interface (API) address of an external service such as a social media service or the like may be designated. Through the external device/service registration unit 222, a user may receive feedback on a proper UI/UX service through his/her own UI device 120 and/or from various external devices and/or services 140 when the occurrence of the concerned context is predicted or recognized.

Further, the UI device 120 includes a feedback registration unit 223 for registering a feedback type such as a text, a sound, vibration, light, etc. desired to be given when a prediction or recognition event corresponding to the occurrence of the concerned context is generated, and a feedback giver 224 for giving the registered feedback type (e.g., displaying a text, making a sound/vibration, turning on a light-emitting diode (LED), etc.) when the prediction or recognition event corresponding to the occurrence of the concerned context is received from the emotion-biological information model management module 130.

In addition, a circumstance extracting and recognizing unit 225 of the UI device 120 extracts current circumstances such as a time slot, a place, a user behavior, an atmospheric temperature, etc. from the UI device 120 itself, and recognizes whether concerned context designated with a circumstance matching the currently extracted circumstance has been registered. To extract semantic attribute values of a place, a time, and a behavior, the UI device 120 may use a built-in timer and a built-in sensor, or information provided by other services (weather application, an address conversion application, etc.) driven in the UI device 120. In an embodiment where the user-wearable information collection device 110 includes a separate circumstance collector 212, a specific circumstance may be received from the circumstance collector 212.

To determine the semantic attribute values (for example, to make pieces of set information match semantic attributes of absolute time when a user sets 'time' with an evening time slot, a dawn time slot, etc.), a technique based on rules or probabilistic inference may be employed.

A voice/biological information feature extractor 226 of the UI device 120 extracts voice/biological information features from a current user voice (acquirable by automatically activating a built-in microphone of the UI device 120) and current user biological information (received from the biological information collector 211) when the circumstance extracting and recognizing unit 225 recognizes that the current circumstance matches the circumstance of the registered concerned context, and transmits the extracted voice/biological information features along with the circumstance to the emotion-biological information model management module 130 through an emotion-biological information model interface 227.

Meanwhile, the emotion-biological information model management module 130 includes an emotion-biological information model manager 231 that reflects concerned context information registered by a user in an emotion-biological information model, and controls the emotion-biological information model to learn both voice/biological information feature generated for emotions and reference statistics of a user's biological information feature according to atmospheric temperatures and user behavior. Further, an emotion recognizer 232 is provided to generate a feature vector to be used in recognizing a user's current emotional state by reflecting reference statistics of biological information according to the user's behavior/atmospheric temperature, from voice/biological response information received from the UI device 120. Further, a concerned-context occurrence probability calculator 233 calculates a concerned-context occurrence probability corresponding to a recognized biological information range and a recognized emotion attribute.

The emotion recognizer 232 and the concerned-context occurrence probability calculator 233 determine a user's biological information range by using the already learned emotion-biological information model and the generated voice/biological information feature information, thereby recognizing the emotional state and calculating the concerned-context occurrence probability. In this case, the concerned-context occurrence probability may reflect a probability to be recognized as a specific emotion label during an emotion recognition process.

The concerned-context event generator 234 compares the calculated concerned-context occurrence probability with a predetermined threshold to determine 'concerned-context occurrence prediction' or 'concerned-context occurrence recognition' and generate each corresponding event. There may be various determination methods, and one of them is to compare a first threshold $thr_1$ for determining the 'occurrence prediction' and a second threshold $thr_2$ for determining the 'occurrence recognition' to thereby predict or recognize the occurrence of the concerned context. For example, it may be designed to predict the occurrence when the concerned-context occurrence probability is higher than the first threshold but lower than the second threshold, and to recognize the occurrence when the probability is higher than the second threshold. Alternatively, it may be designed to determine the occurrence recognition rather than the occurrence prediction when an increasing trend of the probability having a predetermined pattern is detected between the first threshold and the second threshold by considering a probability calculation cycle (e.g., 1 second, 5 seconds, 10 seconds, . . . ). Besides, a predetermined criterion may be made by various methods so as to determine the concerned-context occurrence prediction or recognition.

Meanwhile, as described above, the emotion-biological information model management module 130 (including the emotion-biological information model) may be configured in a separate independent server (including a cloud server) connected via the Internet or a similar network, or may be installed and driven in the UI device 120.

Figure 4:
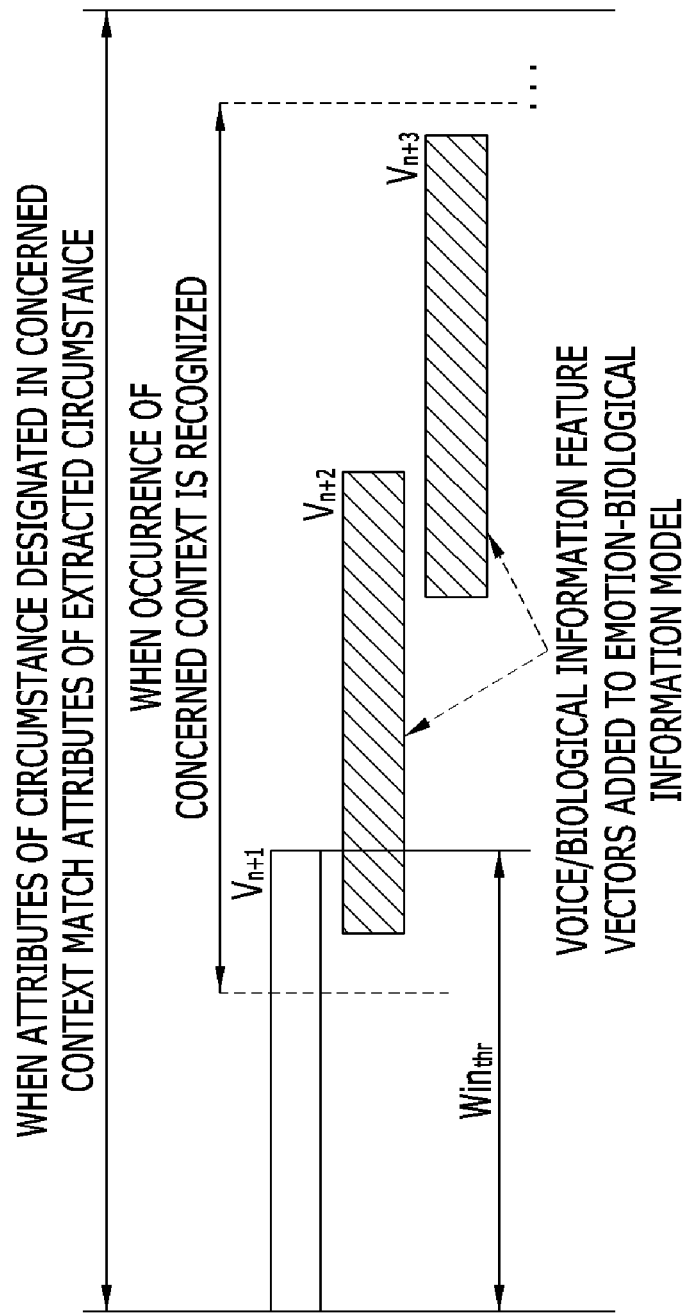
FIG. 4 shows an example of how voice/biological information feature vectors are input to a model for learning the voice/biological information feature vectors.

FIG. 4 shows how voice/biological information feature vectors are input to the emotion-biological information model when these vectors are learned. Schematically, 'extraction of feature vectors' starts when the circumstances (behavior, time, etc.) are matched in the registered concerned context, and 'addition of generated feature vectors to the emotion-biological information model' is implemented when the occurrence of the concerned context is recognized. Detailed descriptions thereof are as follows.

When it is recognized that attributes of circumstantial elements designated in concerned context $c_k$ registered by a user match attributes of circumstantial elements extracted by the UI device 120, user experience (UX) data is extracted as the circumstance and voice/biological information feature vectors in units of sliding window $Win_{thr}$ and transmitted to the emotion-biological information model management module 130. Thus, the emotion-biological information model management module 130 determines the current biological information range based on the voice/biological information feature vectors reconfigured by considering a correlation between a previously learned emotion-biological information model and a circumstance, a behavior and an atmospheric temperature, thereby recognizing a user's emotional state. The occurrence probability of the registered concerned context is calculated to generate a corresponding concerned context event of when the occurrence of the concerned context is predicted or recognized, and collected voice/biological information feature vectors $V_{n+2}$ and $V_{n+3}$ are managed as added to a model for learning the emotion-biological information model when the occurrence of the concerned context is recognized. That is, referring to FIG. 4, the voice/biological information feature vectors $V_{n+2}$ and $V_{n+3}$ are added to the emotion-biological information model (see the hatched portions), but a feature vector $V_{n+1}$ is not added to the emotion-biological information model because the occurrence of the concerned context is not recognized yet. However, the description with reference to FIG. 4 is merely one example, and may alternatively be carried out as intended by those skilled in the art.

Referring back to FIG. 3, the concerned-context event generator 234 of the emotion-biological information model management module 130 generates the occurrence prediction or recognition event as shown in FIG. 4, and the generated event is transmitted to the UI device 120 and/or the external device/service 140 (see FIG. 1) registered by a user with regard to the corresponding concerned context. The event is configured to distinguish an identifier of the concerned context, an occurrence prediction or recognition time, and types of prediction event or recognition event.

Figure 5:
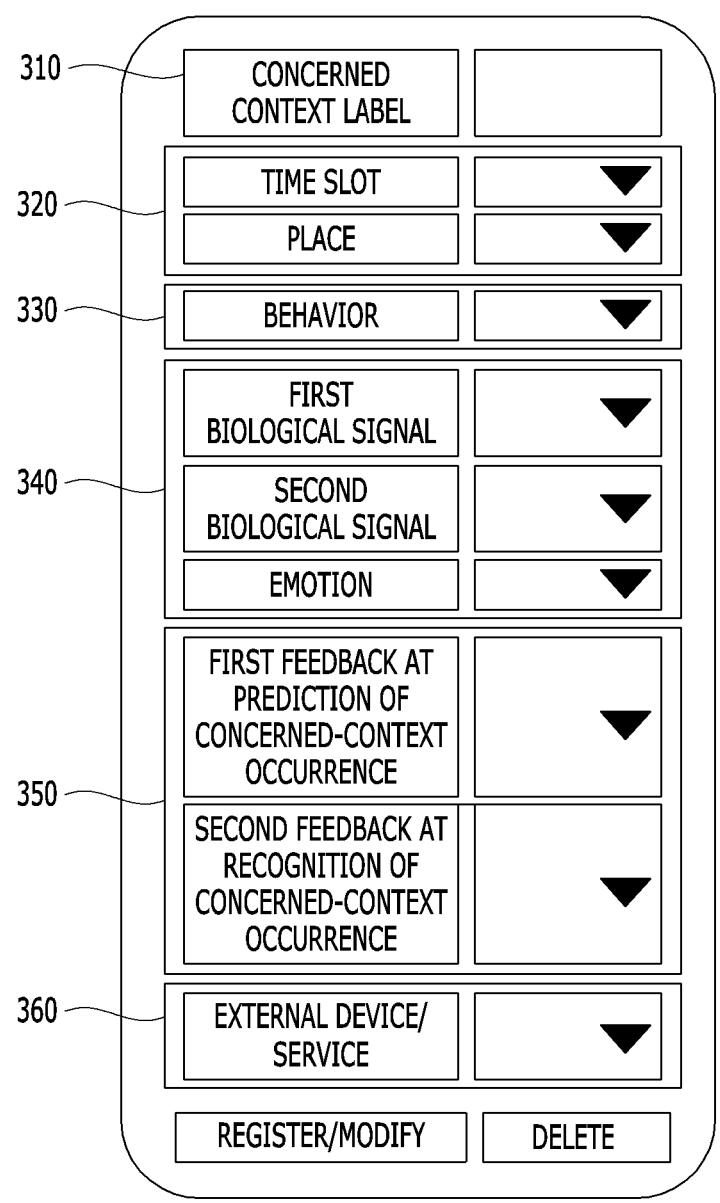
FIG. 5 shows a user interface (UI) screen for registering and modifying concerned context.

FIG. 5 shows a UI screen for registering or modifying concerned context in the UI device 120 (e.g., in the concerned context definer 221). A UI for managing the concerned context may be synchronized with the emotion-biological information model management module 130.

Through the interface shown in FIG. 5, a user may set a concerned context label (310) to be registered or modified (e.g., a concerned context about the user's own emotion, biological information, etc., for instance, 'angry at conference', 'blood pressure goes up in the morning'). Further, among the circumstances of the corresponding concerned context, a time slot and place (320), a user behavior (330), ranges of biological information (or a biological signal) and attributes of an emotion (340) can be set. Further, through the emotion-biological information model, a user may register first feedback to be given when the occurrence of the registered concerned context is predicted (i.e., in response to a prediction event) and second feedback to be given when the occurrence of the registered concerned context is recognized (i.e., in response to a recognition event) (350), and register an external device/service to be used for an interface to receive the feedback when the occurrence prediction or recognition event is generated (360).

Figure 6A:
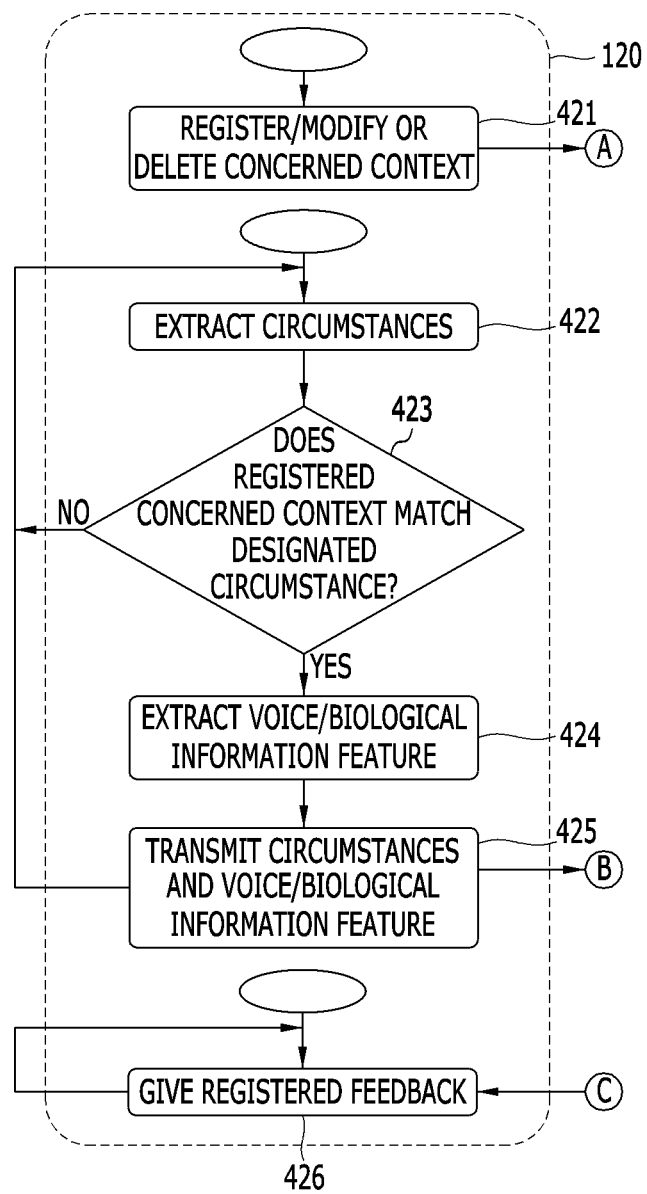

FIGS. 6A and 6B are respectively functional flowcharts between the UI device 120 and the emotion-biological information model management module 130 in the apparatus and method for predicting/recognizing occurrence of personal concerned context according to one embodiment of the present invention. Further, as described above, FIGS. 6A and 6B show not only a process flow diagram in terms of a method, but also function implementing blocks of hardware or software in terms of an apparatus.

A user may register/modify or delete the concerned context through a concerned context UI (e.g., refer to the interface of FIG. 5) of the UI device 120 (421). When a user registers/modifies or deletes the concerned context information, the emotion-biological information model management module 130 updates corresponding concerned context information in the emotion-biological information model (431).

The UI device 120 extracts current circumstances such as a time, a place, a user behavior, an atmospheric temperature, etc. (422), and determines whether concerned context matching the designated circumstance has been registered (423). As described above, the circumstances may be extracted through a sensor and various applications in the UI device 120, and may be acquired from a user wearable device (for example, the circumstance collector 212 of FIG. 3).

When it is recognized (or determined) that the circumstance designated in the registered concerned context matches the current extracted circumstance, a user voice feature and/or a biological information feature is extracted (424). As described above, the user voice feature is extractable from a voice acquired through the microphone of the UI device 120, and the biological information feature is extractable from a biological signal acquired from the user wearable device (for example, the biological information collector 211 of FIG. 3). Along with the circumstance, the extracted voice feature and/or biological information feature are transmitted to the emotion-biological information model management module 130 (425).

The emotion-biological information model management module 130 uses the circumstance and the voice/biological information feature received from the UI device 120 (425) and the reference statistics of the information where user voice/biological information features related to the atmospheric temperature and the behavior have been previously accumulated, thereby determining each attribute range of the user biological information (432), recognizing a current user emotional state, and calculating the concerned-context occurrence probability (433). In this stage (or element) 433 for recognizing a user's emotion and calculating the concerned-context occurrence probability, the voice/biological information feature vector is configured to include appended information using the reference statistics of each biological information managed according to the atmospheric temperature and the behavior in the emotion-biological information model management module 130. For example, the voice/biological information feature received from the UI device 120 may be compared with the reference statistics of the voice/biological information and reconfigured as the feature vector including appended information such as difference, maximum (max), minimum (min), etc. Using the feature information of the already learned emotion-biological information model and the reconfigured feature vector, a user's emotion is recognized in a corresponding concerned context, and the attributes of the emotion elements in the concerned context are determined. The probability information to be classified into a specific emotion calculated in this emotion recognizing process may be reflected in an occurrence probability about the concerned context. In this case, a specific method of recognizing the emotion and calculating the probability through the feature vector and the previously learned model may include machine learning, knowledge base graph model, or combination thereof.

The occurrence probability $P(c_k)$ of the concerned context $c_k$ is calculated by the emotion-biological information model management module 130, using the recognized emotional state information and the biological information range based on the previously learned emotion-biological information model, and using the circumstance and user voice/biological information feature vector may be obtained by the following Equation 1.

$$P(c_k) = \qquad \text{[Equation 1]}$$
$$P(e_j) * tf_e(0|1) * \omega_e + \sum_{n=1}^{N} (fs(s_n) * tf_{s_n}(0|1) * \omega_{s_n}) +$$
$$\sum_{m=1}^{M} (fb(b_m) * tf_{b_m}(0|1) * \omega_{b_m})$$

In brief, the Equation 1 means that a specific concerned-context occurrence probability $P(c_k)$ is calculated by considering all of 1) probability $P(\theta_j)$ that the concerned context designated with a specific emotion element will occur, 2) a function value $fs(S_n)$ reflecting whether attributes of circumstances in the concerned context designated by a user match attributes of extracted circumstances, and 3) a function value $fb(b_m)$ reflecting whether attributes of biological information in the concerned context designated by the user match attributes of extracted biological information. In the first term $tf_e(0|1)$ indicates whether a user designates the attributes of the emotion in the concerned context (e.g., 0 indicates no designation, and 1 indicates a designation), and $\omega_e$ indicates a weight of importance of the emotional attributes. In the second term, $tf_{sn}(0|1)$ indicates whether a user designates the circumstance in the concerned context (e.g., 0 indicates no designation, and 1 indicates a designation), and $\omega_{sn}$ indicates a weight of importance of the circumstance. Since there are a plurality of circumstantial attributes, variables about the circumstances are all added up ($\Sigma$). In the third term, $tf_{bm}(0|1)$ indicates whether a user designates the biological response information in the concerned context (e.g., 0 indicates no designation, and 1 indicates a designation), and $\omega_{bm}$ indicates a weight of importance of the biological information. Since there are also a plurality of attributes of biological response information, variables about the biological response information are all added up ($\Sigma$).

Variables used in the Equation 1 for calculating the occurrence probability $P(c_k)$ of the concerned context $c_k$ are tabulated in a Table 3.

TABLE 3

| | |
|---|---|
| $P(c_k)$ | occurrence probability of specific concerned context $(c_k)$ |
| $P(\theta j)$ | probability that an emotional label $(\theta j)$ will be recognized in the specific concerned context $(c_k)$ |
| $tf_e(0|1)$ | whether an emotional attribute is designated in the specific concerned context $(c_k)$ |
| $\omega_e$ | an emotional weight of emotional element in the specific concerned context $(c_k)$ |
| $fs(S_n)$ | a function value reflecting whether an attribute of the circumstantial element $(S_n)$ in the specific concerned context $(c_k)$ matches an attribute of the extracted circumstantial element $(S_n)$ |
| $tf_{sn}(0|1)$ | whether an attribute of the circumstantial element $(S_n)$ is designated in the specific concerned context $(c_k)$ |
| $\omega_{sn}$ | a weight of the circumstantial element $(S_n)$ in the specific concerned context $(c_k)$ |
| $fb(b_m)$ | a function value reflecting whether an attribute of biological information element $(b_m)$ in the specific concerned context $(c_k)$ matches an attribute of recognized biological information element $(b_m)$ |
| $tf_{bm}(0|1)$ | whether the attribute of the biological information element $(b_m)$ is designated in the concerned context $(c_k)$ |
| $\omega_{bm}$ | a weight of the biological information element $(b_m)$ in the specific concerned context $(c_k)$ |

Referring back to FIGS. 6A and 6B, the emotion-biological information model management module 130 also updates the reference statistics about the voice/biological information features corresponding to the atmospheric temperature and behavior managed therein (i.e., in the emotion-biological information model management module 130) using the voice/biological information features, which are received from the UI device 120 when the circumstances in the concerned context are matched (434).

Next, it is determined whether the concerned-context occurrence probability calculated in the stage (or element) 433 for calculating the user emotion recognition and the concerned-context occurrence probability is higher than or equal to the threshold $thr_1$ to such an extent as to predict the occurrence of the concerned context, or is higher than or equal to the threshold $thr_2$ to such an extent as to recognize the occurrence of the concerned context (435). If determined as such, the concerned context event (i.e., the concerned context occurrence prediction event or the concerned context occurrence recognition event) is generated, and transmitted to the UI device 120 and/or interfaced with the registered external device/service 140 (see FIG. 1) (436).

Meanwhile, when the concerned context occurrence recognition event is generated, the previously extracted voice/biological information feature vector is added to the emotion-biological information model as the voice/biological information feature vector corresponding to the recognized emotion label and the biological information range corresponding to the behavior of the circumstance of the corresponding concerned context and used in relearning the model (437), and the relearning results are transmitted to the UI device 120 so that various types of feedback registered by a user can be implemented in the UI device 120 or the device worn on the user (e.g., the information collection device 110 of FIG. 2)(426).

Figure 7:
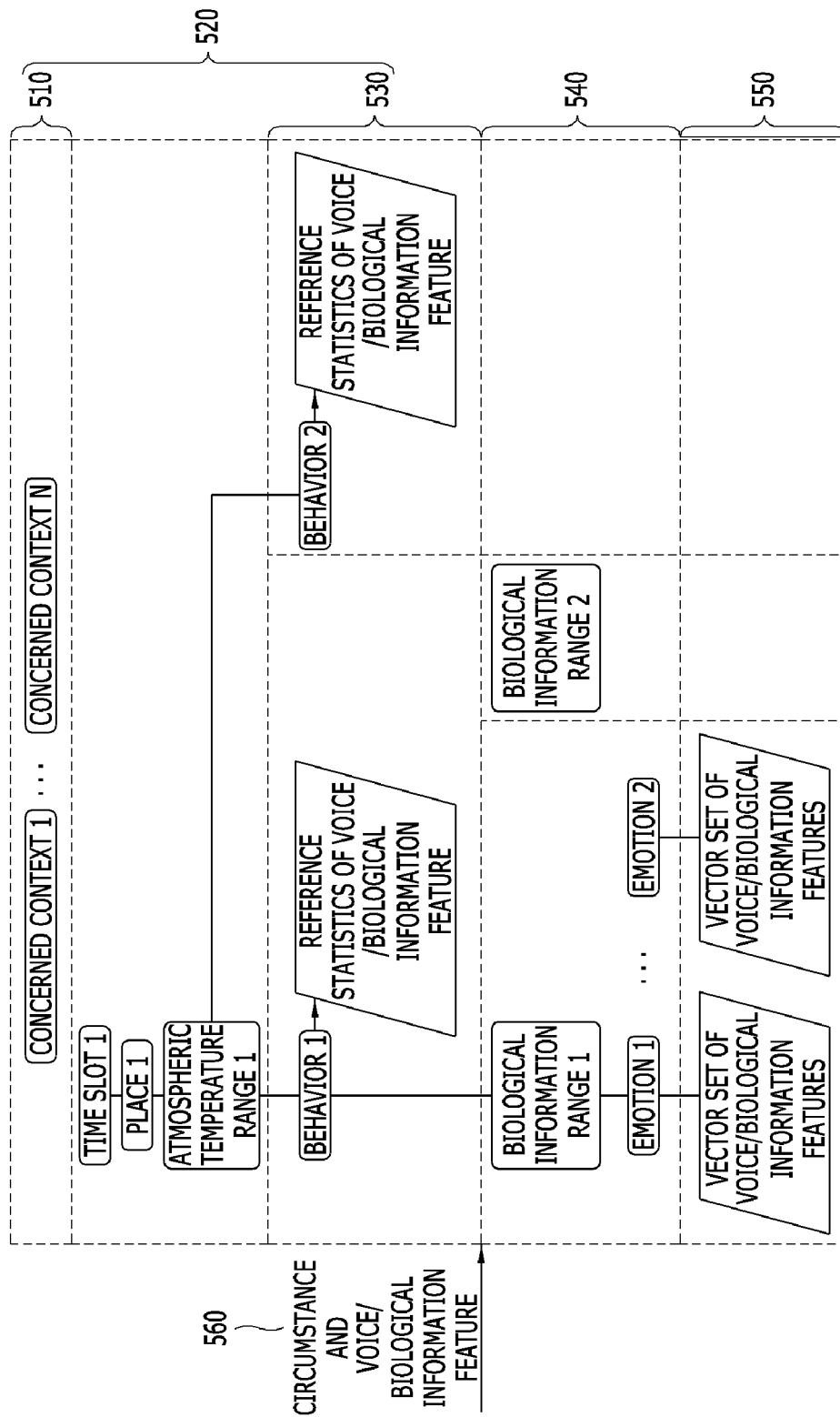
FIG. 7 is a configuration view of an emotion-biological information model.

FIG. 7 is a semantic configuration view of an emotion-biological information model according to the present invention. The emotion-biological information model shown in FIG. 7 refers to not a tangible physical configuration but a semantic configuration for describing the meaning or function of the learning model achievable by a machine learning technique. Through the semantic configuration of FIG. 7, an emotion-biological information learning model of various architectures, such as a convolutional neural network (CNN), a recurrent neural network (RNN), deep learning, a support vector machine, etc. may be materialized by those skilled in the art.

This emotion-biological information model is configured to have a correlation with circumstances 520, such as a time slot, a place, an atmospheric temperature, and a user behavior according to a plurality of registered pieces of concerned context 510, a biological information range and recognized emotion label 540, and a set of voice/biological information feature vectors 550. This model manages statistics 530 of a reference voice/biological information feature according to behavior/atmospheric temperatures to reflect information about the correlation with the user behavior and the atmospheric temperature so as to correctly recognize the emotion based on the circumstance and the voice/biological information feature. The circumstances (the behavior, etc.) and the voice/biological information features 560 received from the terminal (for example, the UI device 120) are configured again into the feature vectors set 550 by using the biological information reference statistics 530, and a user emotional state is recognized based on this previously learned model.

The recognition of the user emotional state is determined in the emotion-biological information model from the voice and the biological response information, and an actual emotional state is recognized through the emotion-biological information model when a user designates the emotional attributes of the emotional elements such as joy and anger in a specific concerned context. Moreover, in the emotion-biological information model, a user's usual emotional change features according to his/her behavior and atmospheric temperature are stored as reference data, and the emotional state is predicted by referring to this user data when data, a behavior, an atmospheric temperature and biological response information are actually input. Accordingly, robust emotional state recognition is possible with regard to a circumstance such as a user behavior, etc.

As described above, points in time when UX data is actually collected and processed are automatically determined according to the attributes of elements in the registered concerned context. That is, a user's voice/biological information features are extracted without user intervention when the circumstances of the registered concerned context are matched, and the feature vector including the voice/biological information feature, extracted when the occurrence of the concerned context is recognized, is added to the emotion-biological information model.

Further, feedback, which is desired to be given when the occurrence of the corresponding concerned context is predicted or recognized, and an external device/service, which is desired to interface with a corresponding event, can be registered by a user as s/he wants.

In conclusion, robust emotion recognition is performed with regard to effects of a user's specific behavior and atmospheric temperature, and an event is generated as the occurrence of the registered concerned context is predicted or recognized, and thus the user can receive proper UI/UX from various devices and services.

Detailed embodiments of the present invention have been described above by way of example. However, the technical scope of the present invention is not limited by these embodiments, but defined in rational interpretation of the appended claims.

What is claimed is:

1. An apparatus for predicting/recognizing occurrence of personal concerned context, the apparatus comprising:
    a user interface device comprising a concerned context definer through which a user designates biological information, emotions, and circumstances and registers concerned context about the user's own biological information change or emotional state; and
    an emotion-biological information model management module comprising an emotion-biological information model manager which reflects information about the concerned context registered by the user in an emotion-biological information model, makes the emotion-biological information model learn from a user voice/biological information feature and reference statistics of the user voice/biological information feature depending on user behavior and atmospheric temperature, and manages the emotion-biological information model, and a concerned-context event generator which generates a concerned-context occurrence prediction event or a concerned-context occurrence recognition event by predicting or recognizing the occurrence of the concerned context registered in the concerned context definer of the user interface device.

2. The apparatus of claim 1, wherein the user interface device further comprises:
    a circumstance extracting and recognizing unit which extracts a current circumstance from the user interface device, and recognizes whether concerned context designated with a circumstance matching the extracted current circumstance has been registered; and
    a voice/biological information feature extractor which extracts a voice/biological information feature from current user voice/biological information and transmits the extracted voice/biological information feature along with the circumstance to the emotion-biological information model management module when the circumstance extracting and recognizing unit recognizes that the current circumstance matches the circumstance of the registered concerned context.

3. The apparatus of claim 1, wherein the user interface device further comprises:
    a circumstance extracting and recognizing unit which extracts a current circumstance from a circumstance received from a user wearable information collection device, and recognizes whether concerned context designated with a circumstance matching the extracted current circumstance has been registered; and
    a voice/biological information feature extractor which extracts a voice/biological information feature from current user voice/biological information and transmits the extracted voice/biological information feature along with the circumstance to the emotion-biological information model management module when the circumstance extracting and recognizing unit recognizes that the current circumstance matches the circumstance of the registered concerned context.

4. The apparatus of claim 1, wherein the user interface device further comprises:
    a feedback registration unit which registers a type of feedback desired to be given when the concerned-context occurrence prediction or recognition event is generated; and
    a feedback giver which gives the registered type of feedback when the concerned-context occurrence prediction or recognition event is received from the emotion-biological information model management module.

5. The apparatus of claim 4, wherein the user interface device further comprises an external device/service registration unit which registers an external device and service to interface with the feedback given when the concerned-context occurrence prediction or recognition event is generated.

6. The apparatus of claim 2, wherein the emotion-biological information model management module further comprises:
    an emotion recognizer which extracts a feature vector to be used for recognizing the user's emotion from the voice/biological information feature received from the user interface device; and
    a concerned-context occurrence probability calculator which calculates an occurrence probability of the concerned context on the basis of the emotion-biological information model and the extracted voice/biological information feature vector.

7. The apparatus of claim 1, wherein the concerned-context event generator of the emotion-biological information model management module uses a threshold for determining occurrence prediction and a threshold for determining occurrence recognition to determine either of concerned-context occurrence prediction or concerned-context occurrence recognition.

8. An apparatus for predicting/recognizing occurrence of personal concerned context, the apparatus comprising:
    a concerned context definer through which a user designates biological information, emotions, and circumstances and registers concerned context about the user's own biological information change or emotional state;

an emotion-biological information model manager which reflects information about the concerned context registered by the user in an emotion-biological information model, makes the emotion-biological information model learn from a user voice/biological information feature and reference statistics of the user voice/biological information depending on user behavior and atmospheric temperature, and manages the emotion-biological information model; and a concerned-context event generator which generates a concerned-context occurrence prediction event or a concerned-context occurrence recognition event by predicting or recognizing the occurrence of the concerned context registered in the concerned context definer.

9. The apparatus of claim 8, further comprising:
a circumstance extracting and recognizing unit which extracts a current circumstance of the user, and recognizes whether concerned context designated with a circumstance matching the extracted current circumstance has been registered; and a voice/biological information feature extractor which extracts a voice/biological information feature from current user voice/biological information when the circumstance extracting and recognizing unit recognizes that the current circumstance matches the circumstance of the registered concerned context.

10. The apparatus of claim 8, further comprising:
a circumstance extracting and recognizing unit which extracts a current circumstance from a circumstance received from a user wearable information collection device, and recognizes whether concerned context designated with a circumstance matching the extracted current circumstance has been registered; and a voice/biological information feature extractor which extracts a voice/biological information feature from current user voice/biological information when the circumstance extracting and recognizing unit recognizes that the current circumstance matches the circumstance of the registered concerned context.

11. The apparatus of claim 8, further comprising:
a feedback registration unit which registers a type of feedback desired to be given when the concerned-context occurrence prediction or recognition event is generated; and a feedback giver which gives the registered type of feedback when the concerned-context occurrence prediction or recognition event is generated in the concerned-context event generator.

12. The apparatus of claim 11, further comprising an external device/service registration unit which registers an external device and service to interface with the feedback given when the concerned-context occurrence prediction or recognition event is generated.

13. The apparatus of claim 9, further comprising:
an emotion recognizer which extracts a feature vector to be used for recognizing the user's emotion from the voice/biological information feature; and a concerned-context occurrence probability calculator which calculates an occurrence probability of the concerned context on the basis of the emotion-biological information model and the extracted voice/biological information feature vector.

14. The apparatus of claim 8, wherein the concerned-context event generator uses a threshold for determining occurrence prediction and a threshold for determining occurrence recognition to determine either of concerned-context occurrence prediction or concerned-context occurrence recognition.

15. A method of predicting/recognizing occurrence of personal concerned context, the method comprising:
designating, by a user, biological information, emotions, and circumstances and registering concerned context about the user's own biological information change or emotional state;

reflecting information about the concerned context registered by the user in an emotion-biological information model, making the emotion-biological information model learn from at least one of user voice and biological information features and reference statistics of user voice/biological information feature, and managing the emotion-biological information model; and generating a concerned-context occurrence prediction event or a concerned-context occurrence recognition event by predicting or recognizing the occurrence of the registered concerned context.

16. The method of claim 15, further comprising:
extracting a current circumstance of the user, and recognizing whether concerned context designated with a circumstance matching the extracted current circumstance has been registered; and extracting a voice/biological information feature from current user voice/biological information when it is recognized by the extraction and recognition of the circumstance that the current circumstance matches the circumstance of the registered concerned context.

17. The method of claim 16, further comprising:
extracting a feature vector to be used for recognizing the user's emotion from the voice/biological information feature; and calculating an occurrence probability of the concerned context on the basis of the emotion-biological information model and the extracted voice/biological information feature vector.

18. The method of claim 15, wherein the generation of the concerned-context occurrence prediction or recognition event further comprises giving feedback to the user when the concerned-context occurrence prediction or recognition event is generated.

19. The method of claim 15, wherein the generation of the concerned-context occurrence prediction or recognition event further comprises using a threshold for determining occurrence prediction and a threshold for determining occurrence recognition to determine either of concerned-context occurrence prediction or concerned-context occurrence recognition.

* * * * *